United States Patent [19]

Newman et al.

[11] Patent Number: 5,006,642

[45] Date of Patent: Apr. 9, 1991

[54] PURIFICATION OF VON WILLEBRAND FACTOR BY AFFINITY CHROMATOGRAPHY

[75] Inventors: Jack Newman, Burke; David L. Farb, Woodbridge, both of Va.

[73] Assignee: Rhone-Poulenc Rorer Pharmaceuticals Inc., Fort Washington, Pa.

[21] Appl. No.: 205,881

[22] Filed: Jun. 13, 1988

Related U.S. Application Data

[62] Division of Ser. No. 67,990, Jun. 29, 1987, Pat. No. 4,774,323.

[51] Int. Cl.$^5$ .................. C07K 15/06; C07K 3/18; C07K 3/28
[52] U.S. Cl. ...................... 530/383; 530/380; 530/381; 530/350; 530/413; 530/427
[58] Field of Search ............... 530/380, 381, 383, 350, 530/413, 427

[56] References Cited

U.S. PATENT DOCUMENTS

| Re. 32,011 | 10/1985 | Zimmerman | 424/101 |
| 4,278,594 | 7/1981 | Amrani | 530/383 |
| 4,710,381 | 12/1987 | Kunicki | 424/101 |
| 4,774,323 | 9/1988 | Newman et al. | 530/383 |

FOREIGN PATENT DOCUMENTS 3237512 4/1984 Fed. Rep. of Germany .

OTHER PUBLICATIONS

Olson et al., 1983, *Thrombosis Research*, 32:115–122.
Thorell et al., 1984, *Thrombosis Research*, 35:431–450.
Patent Abstract, Dialog File 357, DBA Accession No.: 84–06133, DE 3,237,512, 1984.
Orthner et al., 1984, J. Lab. Clin. Med., 104:817–827.
Olson et al., 1977, J. Lab. Clin. Med. 89(6):1278–1294.
Kazuhiro Nakanishi, Agri Biol. Chem., 43(12), 2507–2513, (1979).
A. N. Izmailov, Chem. Abstr., 80,105487u, (1974).
Claudine Mazurier, Vox Sang., 52:265–271 (1987).
Teresa Leszczynska, Chem. Abs., 93,90743s, (1980).
Emilio Rivas, Chem. Abs., 97,123233p, (1982).
Vladimir Gusmari, Chem. Abs., 95,146329Z, (1981).

*Primary Examiner*—Margaret Moskowitz
*Assistant Examiner*—Keith C. Furman
*Attorney, Agent, or Firm*—Imre (Jim) Balogh; James A. Nicholson

[57] ABSTRACT

A method of preparing von Willebrand Factor by disassociating it from a chaotropic agent in solution therewith and preferably treating the same under controlled temperature either in liquid or lyophilized form.

12 Claims, No Drawings

PURIFICATION OF VON WILLEBRAND FACTOR BY AFFINITY CHROMATOGRAPHY

This application is a division of copending application Ser. No. 067,990, filed June 29, 1987, now U.S. Pat. No. 4,774,323.

BACKGROUND OF THE INVENTION

1. Field of the Invention

This invention relates to a method for preserving the activity of the von Willebrand Factor. More particularly it relates to a method of separating and purifying von Willebrand Factor, and providing an active protein for the treatment of the von Willebrand's disease.

Von Willebrand Factor (hereinafter vWF) circulates in plasma complexed with Factor VIII procoagulant activity protein (hereinafter VIII). The complex is believed to have two biologic functions: vWF corrects defects of platelet function in von Willebrand's disease, and VIII corrects the clotting defect in hemophilia. vWF exists in plasma as a series of multimeric forms of a protein ranging in molecular weight from about $1 \times 10^6$ to about $20 \times 10^6$ Daltons. Von Willebrand disease is characterized by the absence or reduced level of the higher molecular weight forms of this protein and is manifest by prolonged bleeding due to the inability of platelets to aggregate and initiate clotting at the wound cite. Traditionally, treatment of bleeding episodes caused by this disease consisted of the administration of cryoprecipitate prepared from human plasma containing normal vWF. This treatment exposed the patient to other coagulation factors and other plasma proteins, particularly fibronectin and fibrinogen. Repeated administration of extraneous proteins has been shown to be deleterious to the health of the patient because of changes brought about in blood viscosity. Treatment with cryoprecipitate also exposed the patient to infectious viruses, such as hepatitis viruses and AIDS viruses which may be present in the donor's plasma.

Commercial concentrates of Factor VIII prepared from plasma by cryoprecipitation of the vWF/Factor VIII complex, followed by purification and concentration, have not been proven to be as effective as expected in the treatment of von Willebrand's disease. The therapeutic inadequacy of these preparations has been in part attributed to the absence of sufficient potency of higher molecular weight forms of vWF that are believed to be essential for the restoration of hemostatis when bleeding occurs in vWF deficient patients. There has been no attempt to treat von Willebrand patients with isolated and purified vWF because the isolation of a biologically active vWF in large quantities could not be carried out with existing technology. With the development of monoclonal and polyclonal antibodies specific to vWF, such technology has become available.

2. Description of the Prior Art

U.S. Pat. No. 4,361,509 and U.S. Pat. No. RE. 32,011 issued to Zimmerman et al. disclose a method for the preparation of high purity VIII comprising the steps of:

(1) adsorbing the VIII/vWF complex from a plasma or commercial concentrate source onto agarose beads bound to a monoclonal antibody specific to vWF;

(2) eluting VIII with a salt solution;

(3) adsorbing the eluted VIII on aminohexyl agarose column; and (4) eluting the VIII with a salt solution.

The immunoadsorbent column described in said references is regenerated by eluting vWF with 3M aqueous sodium thiocyanate (NaSCN) solution. This step results in the preservation of the monoclonal antibody on the column so that the same may be used again in the process. The vWF/sodium thiocyanate solution is discarded as a waste.

The present invention utilizes this waste material as a source of vWF although it is not limited thereto. In the process of developing the invention, it was discovered that biological activity of vWF is normally lost as a result of its elution from the antibody column with sodium thiocyanate solution. Illustrative is the result obtained on material produced according to the teaching of the cited references, description of which follows.

Normal human plasma was collected from normal plasmapheresis donors and diluted with 1/6 volume of 4% sodium citrate. The citrated plasma was immediately frozen and later pooled with additional citrated plasmas and allowed to thaw. Cryoprecipitable proteins were isolated at 0°-2° C. by cold centrifugation of the thawed plasma pool. Approximately 100 g of cryoprecipitate was collected from 100 liters of pooled, citrated plasma. The cryoprecipitate was resuspended at 37° C. in 4 volume of water containing 60 mM glycine and 40 mM sodium chloride at pH 7, then clarified with Al(OH)$_3$ and by centrifugation. Four liters of clarified cryosolution were passed over a 10×15 cm column of anti-vW Sepharose. The nonbound proteins were washed through the column with a solution of lysine (0.1 M), histidine (0.02 M) and NaCl (0.15 M) at pH 7. Factor VIII activity was eluted with 0.25 M CaCl$_2$. The vWF proteins were eluted with 3 M NaSCN.

The one liter immunoaffinity column yielded between 500 and 800 ml of thiocyanate solution containing between 170 and 540 mg von Willebrand protein, having antigenic and molecular properties similar to the unpurified von Willebrand protein found in cryoprecipitate. Measurement using the ristocetin cofactor, platelet agglutination test, however, showed that very little activity was preserved during the elution with 3M NaSCN.

Similar results have been reported by Hornsey, et al. (Thrombosis and Haemostasis - F.K. Schattauer Verlag GmbH, Stuttgart 57 (1) 102-105 (1987).

It is clear that such activity is not quite adequate for therapeutic use and there exists a need for a method for preserving vWF activity in the by-product or waste product obtained by the method of separating and purifying VIII.

SUMMARY OF THE INVENTION

The present invention relates to a method of separating the vWF from a solution containing the factor and a chaotropic agent, such as sodium thiocyanate, formulating and lyophilizing the same for therapeutic use. Prior to formulating or after reconstituting the lyophilized factor for injection, a heating step is preferably employed to increase the potency of the vWF.

The vWF is obtained as a bi-product of the process for ultrapurification of Factor VIII to obtain VIII as disclosed, for example in U.S. Pat No. 4,361,509 and U.S. Pat. No. Re 32,011 which are incorporated herein by reference. The ultrapurification of Factor VIII comprises:

(a) adsorbing VIII/vWF complex from concentrate source onto a solid phase backbone containing monoclonal or polyclonal or cocktail of monolanal anti-vWF antibodies covalently linked to said solid phase backbone;
(b) washing unbound proteins from the solid phase;
(c) eluting VIII with a chaotropic solution; and
(d) eluting vWF from the solid phase with a chaotropic solution.

Immediately following the elution, the vWF is separated from the chaotropic agent to prevent degradation of the vWF. The separation can be effected by desalting, dialyzation or precipitation. After formulating, the solution is sterile filtered and lyophilized for storage.

While the vWF of the present invention is suitable for therapeutic and other purposes, it was surprisingly discovered that an additional process step, termed mild incubation step, further enhances the factor's activity. This incubation is accomplished by maintaining the vWF at a temperature of about 20° C. to 55° C. for about 1 to 30 hours, more preferably about 30° C. to 55° C. for 5 to 15 hours, and most preferably at 45° C. to 55° C. for 1 to 5 hours.

DETAILED DESCRIPTION OF THE INVENTION

The main objects of the present invention include: (a) the manufacture of a therapeutically effective vWF from waste material which heretofore has been discarded as a bi-product of the process for the manufacturing of VIII; and (b) increasing the platelet agglutination activity of vWF by subjecting the same to a controlled temperature environment.

The starting material used in the process of the present invention is the waste solution of a chaotropic agent/vWF. Said chaotropic agent dissociates the vWF from the antibodies covalently linked to a solid phase backbone. The preferred chaotropic agent is sodium thiocyanate in the range of from about 0.5 M to about 5.0 M, however, other agents may be used as well including ethylene glycol, lithium chloride, potassium iodide, urea, ethylamine, ethanolamine, ethylenediamine, diaminohexane, glycerol, dimethylaminopropylamine and combinations thereof. To obtain this starting material, processes known and used by the prior art can be utilized including that disclosed by the above denoted references.

The process leading to the chaotropic agent/vWF solution is as follows:

Cryoprecipitate, obtained from human or animal plasma or commercial concentrate, containing from about 2,000 to about 40,000 units of VIII per liter of column matrix and from about 8,000 to about 80,000 units of vWF per liter of column matrix is reconstituted in a glycine-sodium chloride solution. The solution is then treated with aluminum hydroxide gel in order to remove vitamin-K dependent coagulation factors. The cryoprecipitate solution is then introduced into a column containing anti-vWF antibodies covalently linked to a solid phase backbone having reactive chemical groups available to bind the antibodies. The amount of antibody used will vary depending on its affinity, however, about 1 gram of antibody per liter of solid phase backbone is required. The solid phase consists of agarose, SEPHADEX, microporous glass, membranes or other solid substances with reactive chemical groups An example of such solid phase is 2B SEPHAROSE sold by Pharmacia, Inc. To effect the covalant linkage between the solid phase and the antibodies, reagents, such as cyanogen bromide, triazine, and hydrazine may be used. The following defines substances referred to by trademarks: SEPHADEX refers to cross-linked dextrans also known as polidexide and poly[(2-diethylamino)ethyl]polyglycerylene dextran hydrochloride (The Merck Index, Tenth Edition, #7426). SEPHADEX G-25 is an extensively cross-linked form of SEPHADEX used for the separation of low-molecular-weight substances, such as sugars and peptides (Molecular Biology of Human Proteins, Schultze, H.E. and Heremans, J.F., Vol. 1, Elsevier Publishing Co., (1966) 290-299. POLYSORBATE 80 is polyoxyethylene(20-)sorbitan mono-oleate (The Merck Index, Tenth Edition, #7455).

From a cryoprecipitate containing 10,000 units of VIII and 40,000 units of vWF per liter of column matrix about 8-9,000 units of VIII and about 30,000 units of vWF per liter of column matrix will bound to the column. The unbound proteins, including fibronectin and fibrinogen, are washed from the column using a buffer solution containing about 0.0025 to 0.05 M histidine (buffering agent), 0.05 to 2.5 M NaCl (solubilizing agent) and 0.05 to 0.5 M lysine (stabilizer against plasmin and plasminogen proteolytic enzymes that tend to degrade VIII and vWF).

Factor VIII then eluted from the column using 0.25 to 2 M calcium chloride solution or solutions of other similarly effective chaotropic agents.

The column is next treated with a 0.50 to 5 M solution of a chaotropic agent, preferably sodium thyocianate, to dissociate vWF from the antibodies and, at the same time, to regenerate the column for further use.

Having attained the vWF in the chaotropic solution, it is of the utmost importance to immediately separate the vWF to prevent its rapid degradation. Separation can be effected by desalting, precipitation and dialyzation.

The desalting process comprises: transferring the vWF/chaotropic agent solution onto a desalting column, such as SEPHADEX G-25, which has previously been equilibrated with a buffer solution containing from about 0.01 to about 0.5 M NaCl and about 1 to about 10 mM of histidine; eluting vWF with the same buffer used to equilibrate the column; sterile filtering the solution; and lyophilizing the vWF solution.

Separation of vWF from the chaotropic agent can be effected by dialyzing against a buffer solution, described under the desalting process, at neutral or close to neutral pHs using state of the art techniques. After dialyzation, the vWF is sterile filtered, formulated, and lyophilized.

Precipitation of vWF can be accomplished by using precipitating agents, such as polyethylene glycol (PEG) having a molecular weight of from 4,000 to 25,000, ammonium sulfate and the like. The concentration of PEG is about 6% to 15% w/w, while that of ammonium sulfate is about 25% to 50% w/w. The precipitate is then isolated by centrifugation and the vWF so obtained dissolved in a buffer containing from about 0.01 to about 0.5 M Tris and 0.01 to about 1.5 M NaCl at a close to neutral pH. The solution is then treated as described above.

The lyophilized factor can then be reconstituted when needed for injection. It is preferable to subject the reconstituted vWF to controlled heat treatment to increase its activity as above-described. Alternatively, the heat treatment may be carried out prior to lyophilization.

The following examples will further illustrate the invention.

The platelet-ristocetin assay being referred to in the examples is essentially the assay method described in Thrombos. Diathes. haemorrh. (Stuttg.), 1975, 34, 306–308, except for the modification that we use: commerical, lyophilized fixed platelet; normal pooled plasma at 1 (100%), 1 (50%) and 1 (25%) dilution to prepare a standard curve; and plasma and vWF preparation in a buffer of pH 7.0.

EXAMPLE 1

A one liter column of anti-vWF Agarose was saturated with a cryoprecipitate solution as described in the prior art. It was washed with 4 volumes of fresh buffer (0.15 M NaCl, 0.1 M lysine, 0.02 M histidine, pH7), then eluted with 2 volumes of 0.25 M $CaCl_2$ followed by 2 volumes 3 M NaSCN. The eluted NaSCN/protein solution (450 ml) was dialyzed for 18 hours against 5 liters 0.05 M NaCl, 10 mM histidine, at pH 7.2. The low salt solution containing 0.23 mg/ml protein, was heated at 45° C. for 4 hours. The agglutination activity increased from 0.1 unit/ml to 15 units/ml.

EXAMPLE 2

The vWF protein was purified as described in Example 1 and 480 ml of the eluted NaSCN protein was desalted over a 10×20 cm column of SEPHADEX G-25 which was previously equilibrated with a solution of 0.05 M NaCl, and 5 mM histidine at pH 7.3. The protein was then eluted in a 510 ml volume free of NaSCN. The desalted vWF solution containing 0.3 mg/ml was frozen and dried by lyophilization in 30 ml aliquots using 50 ml vials. The dried vials were sealed under vacuum and stored at room temperature for up to 6 months. They were reconstituted with 5 ml water to yield a clear solution containing 1.8 mg of vWF/ml and 1.5 units of vWF/ml . One of the reconstituted vials was heated at 50° C. for 2 hours. The activity of vWF was found to increase the activity to 62 units/ml.

EXAMPLE 3

VWF protein was purified and desalted as in Example 2. A solution volume of 780 ml, containing 0.24 ng of vWF/ml was heated at 50° C. for 2 hours to increase the agglutination activity from 0.5 to 19 units/ml. The solution was then filtered through 0.22 um membranes and 30 ml aliquots were placed into separate 50 ml vials for freeze drying as in Example 2. The dried and sealed vials were stored for 3 months and yielded 90 units of vWF/ml when reconstituted with 5 ml of water.

EXAMPLE 4

A 1 M solution of the NaCl was added to cryosolution prior to purification of the vWF proteins as described in Example 1. The eluted NaSCN protein was desalted in a 800 ml volume as in Example 2, then formulated with 0.5% POLYSORBATE 80 and 2% mannitol to aide filtration and lyophilization. The solution was sterilized through a 0.22 um membrane filter and freeze dried in 30 ml aliquots. Upon reconstitution with 5 ml water, a solution containing 3.1 mg of vWF/ml and 2 units of vWF/ml was reactivated by heat treatment at 52° C. for 1.5 hours to yield 140 units of vWF/ml.

EXAMPLE 5

Sufficient amount of $Na_2SO_4$ was added to cryosolution to give a 0.3 M $Na_2SO_4$ solution prior to purification of the vWF proteins described in Example 4. An 850 ml volume was collected from the desalting column and formulated with 0.5% POLYSORBATE 80 and 2% mannitol. The formulation was then heated at 50° C. for 2 hours. A solution containing 0.77 mg of vWF/ml and 60 units of vWF/ml was then filtered and lyophized as described in Example 4.

EXAMPLE 6

Sodium thiocyanate eluate from the anti-vWF affinity column was fed directly onto a SEPHADEX G-25 column equilibrated with 0.05M Tris (hydroxymethyl) aminomethane and 0.15M NaCl buffer at pH 7.1. To the SEPHADEX G-25 eluate was added dropwise, saturated ammonium sulfate adjusted to pH 7.1 in one case and to pH 4.5 in another to bring the final concentration of ammonium sulfate to 50% in the eluate. After 30 minutes at room temperature both preparations were collected by centrifugation and dissolved in 0.05M Tris 0.15M NaCl at pH 7.1. An aliquot of the pH 7.1 ammonium sulfate mixture was kept overnight at 4° C. and then treated in the same way. All of the reconsituted precipates retained vWF activity as measured by the platelet-ristocetin assay.

EXAMPLE 7

Sodium thiocyanate eluate from anti-vWF affinity column was fed directly onto a SEPHADEX G-25 column to remove the sodium thiocyanate and effect an exchange for 0.05M Tris (hydroxymethyl) aminomethane, 0.15 M sodium chloride buffer, at pH 6.3. 12 grams of POLETHYLENE glycol (PEG) 4000/100 ml eluate (10 grams of PEG 6000/100 ml eluate) was then added and the mixture stirred for 30 minutes at room temperature. The precipitate so formed was isolated by centrifugation, dissolved in 0.05M Tris - 0.15M NaCl buffer, at pH 7.25 at 1/10 the volume of the initial G-25 eluate. The vWF activity was present in this solution as measured by the platelet-ristocetin assay.

Analytical characterization of vWF solution showed that platelet agglutination activity gradually increased at room temperature and this increase was amplified by increasing the temperature and prolonging the time of incubation. Analytical characterization has also shown that the molecular distribution and binding properties of vWF were unaltered under these conditions. The data shown in Tables I and II are representative of that obtained according to the present invention.

TABLE I

| | Yield and Specific Activity of vWF | | |
|---|---|---|---|
| Sample | vWF Total Units | Yield % | Specific Activity Units/mg |
| Cryoprecipitate Solution | 44,451 | 100 | 0.498 |
| Unbound Pool | 10,373 | 23.34 | 0.118 |
| vWF Bound to MoAb Column | 34,078 | 76.66 | — |
| Lyophilized vWF Product | 18,990 | 42.72 | 48.20 |

TABLE II

| | At Recovery | | At Incubation | | | |
|---|---|---|---|---|---|---|
| Sample | Unit/ml | Specific Activity Unit/mg | Unit/ml | Specific Activity Unit/mg | At °C. Temp. | At Time/Hrs. |
| 1 | 2.49 | 3.77 | 46.50 | 70.45 | 37 | 25 |
| | | | 34.80 | 52.72 | RT | 25 |
| | | | 54.36 | 82.31 | 37 | 30 |
| 2 | 1.77 | — | 12.33 | — | 37 | 24 |
| 3 | 1.70 | — | 11.50 | — | 37 | 24 |
| 4 | 1.50 | 3.00 | 16.75 | 33.50 | 45 | 1 |
| | | | 20.40 | 40.80 | 45 | 2 |
| | | | 18.80 | 37.60 | 45 | 4 |
| | | | 16.80 | 33.60 | 52 | 1 |
| | | | 21.10 | 42.20 | 52 | 2 |
| | | | 16.90 | 33.80 | 52 | 5 |
| 5 | 1.05 | — | 3.45 | — | 25 | 2 |
| | | | 23.20 | — | 25 | 24 |
| 6 | 1.97 | 0.47 | 3.80 | 0.91 | 25 | 4 |
| | | | 18.80 | 4.48 | | overnight |

Caption: Increase in vWF Activity

What is claimed is:

1. In a method for increasing the therapeutic activity of von Willebrand Factor wherein an essentially purified von Willebrand Factor is obtained by adsorbing a Factor VIII/von Willebrand Factor complex obtained from plasma or commercial concentrate source onto particles bound to a monoclonal or polyclonal antibody specific to von Willebrand Factor;

first eluting Factor VIII from said particles;

next eluting von Willebrand Factor from said particles by washing said particles with a 0.05 M to 5 M aqueous solution of a chaotropic agent; and separating the von Willebrand factor from said chaotropic agent, the improvement which comprises: incubating said essentially purified von Willebrand Factor at a temperature of 20° C. to 55° C. for 1 to 30 hours.

2. The method of claim 1 wherein said von Willebrand Factor is incubated in a liquid state.

3. The method of claim 1 wherein said purified von Willebrand Factor is lyophilized subsequently to the incubating step.

4. The method of claim 1 wherein said separating step comprises: transferring a freshly obtained aqueous solution of von Willebrand Factor/chaotropic agent onto a desalting column to effect adsorption of said chaotropic agent thereto; and eluting the von Willebrand Factor therefrom by a buffer solution at a pH of 6.5 to 7.5.

5. The method of claim 1 wherein said separating step comprises:

dialyzing said aqueous solution against a buffer solution at a pH of 6.5 to 7.5 to obtain a von Willebrand Factor/buffer solution.

6. The method of claim 1 wherein said separating step comprises:

precipitating the von Willebrand Factor by a precipitating agent;

isolating the von Willebrand factor; and dissolving said von Willebrand Factor in a buffer solution at a pH of 6.5 to 7.5.

7. In a method for increasing the therapeutic activity of von Willebrand Factor wherein an essentially purified von Willebrand Factor is obtained by adsorbing a Factor VIII/von Willebrand Factor complex obtained from plasma or commercial concentrate source onto particles bound to a monoclonal or polyclonal antibody specific to von Willebrand Factor;

first eluting Factor VIII from said particles;

next eluting von Willebrand Factor from said particles by washing said particles with a 0.05 M to 5 M aqueous solution of a chaotropic agent; and separating the von Willebrand Factor from said chaotropic agent, the improvement which comprises: incubating said essentially purified von Willebrand Factor at a temperature of 30° C. to 55° C. for 5 to 15 hours.

8. The method of claim 7 wherein said von Willebrand Factor is incubated in a liquid state.

9. The method of claim 7 wherein said purified von Willebrand Factor is lyophilized subsequently to the incubating step.

10. In a method for increasing the therapeutic activity of von Willebrand Factor wherein an essentially purified von Willebrand Factor is obtained by adsorbing a Factor VIII/von Willebrand Factor complex obtained from plasma or commercial concentrate source onto particles bound to a monoclonal or polyclonal antibody specific to von Willebrand Factor;

first eluting Factor VIII from said particles;

next eluting von Willebrand Factor from said particles by washing said particles with a 0.05 M to 5 M aqueous solution of a chaotropic agent; and separating the von Willebrand Factor from said chaotropic agent, the improvement which comprises: incubating said essentially purified von Willebrand Factor at a temperature of 45° C. to 55° C. for 1 to 5 hours.

11. The method of claim 10 wherein said von Willebrand Factor is present in a liquid state.

12. The method of claim 10 wherein said purified von Willebrand Factor is lyophilized subsequently to the incubating step.

* * * * *